United States Patent
Han et al.

(10) Patent No.: US 11,248,221 B2
(45) Date of Patent: Feb. 15, 2022

(54) AGARASE-3,6-ANHYDRO-L-GALACTOSIDASE-ARABINOSE ISOMERASE ENZYME COMPLEX AND METHOD FOR PRODUCTION OF TAGATOSE FROM AGAR USING THE SAME

(71) Applicant: Korea University Research and Business Foundation, Seoul (KR)

(72) Inventors: Sung Ok Han, Seoul (KR); Da-Woon Jeong, Seoul (KR); Jeong Eun Hyeon, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/843,124

(22) Filed: Apr. 8, 2020

(65) Prior Publication Data

US 2021/0009982 A1  Jan. 14, 2021

(30) Foreign Application Priority Data

Feb. 20, 2019 (KR) .................. 10-2019-0019901

(51) Int. Cl.
| | | |
|---|---|---|
| *C12P 7/26* | (2006.01) | |
| *C12N 9/90* | (2006.01) | |
| *C12N 9/24* | (2006.01) | |
| *C12N 9/38* | (2006.01) | |
| *C07K 14/195* | (2006.01) | |

(52) U.S. Cl.
CPC .............. *C12N 9/90* (2013.01); *C07K 14/195* (2013.01); *C12N 9/2402* (2013.01); *C12N 9/2468* (2013.01); *C12P 7/26* (2013.01); *C12Y 302/01059* (2013.01); *C12Y 302/01081* (2013.01); *C12Y 503/01004* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 2015/0167030 A1* | 6/2015 | Mazzoli | C12P 7/56 435/139 |
| 2016/0186156 A1* | 6/2016 | Bayer | C12N 9/2437 435/99 |
| 2017/0275653 A1* | 9/2017 | Bomble | C07K 14/195 |
| 2021/0009982 A1* | 1/2021 | Han | C12N 9/2402 |

OTHER PUBLICATIONS

Gen Bank Accession No. BAB79291.1, published Dec. 15, 2001 (Year: 2001).*

(Continued)

*Primary Examiner* — Richard C Ekstrom
(74) *Attorney, Agent, or Firm* — NSIP Law

(57) ABSTRACT

The present disclosure relates to an enzyme complex of arabinose isomerase, agarase and 3,6-anhydro galactosidase and a method for producing tagatose by degrading agar using the same. By using the enzyme complex according to the present disclosure, agar obtained from marine biomass can be degraded effectively and useful physiologically active substances such as tagatose can be obtained effectively therefrom.

15 Claims, 3 Drawing Sheets
Specification includes a Sequence Listing.

(56) References Cited

OTHER PUBLICATIONS

Geneseq Accession No. AZL47754, published Sep. 15, 2011 (Year: 2011).*
Geneseq Accession No. BFG19550, published Jun. 28, 2018 (Year: 2018).*
Uni Prot Accession No. ARAA_LACSS, published Nov. 22, 2005 (Year: 2005).*
Nguyen et al., "Biochemical properties of L-arabinose isomerase from Clostridium hylemonae to produce D-tagatose as a functional sweetener", PLOS One, 13(4): e0196099, https://doi.org/10.1371/journal/pone.0196099; Apr. 23, 2018 (Year: 2018).*
Ashgar et al., "Identification and biochemical characterization of a novel cold-adapted 1,3-alpha-3,6-L-galactosidase, Ahg786, from Gayadomonasjoobiniege G7", Applied Microbiology and Biotechnology, vol. 102, pp. 8855-8866; Aug. 20, 2018 (Year: 2018).*
Chen et al., "Molecular cloning, expression , and functional characterization of the beta-agarase AgaB-4 from Paenibacillus agarexedens", AMB Express, 8:49; Mar. 28, 2018 (Year: 2018).*
Bayer et al., "The cellulosome—a treasure-trove for biotechnology", Trends in Biotechnology, vol. 12, No. 9, pp. 379-386, 1994 (Year: 1994).*
Geneseq Accession No. BAE46028, published Dec. 6, 2012 (Year: 2012).*
Bayer et al., "The Cellulosomes: Multienzyme Machines for Degradation of Plant Cell Wall Polysaccharides," Annual Review of Microbiology, 2004, vol. 58, pp. 521-554.

\* cited by examiner

[FIG. 1A]            [FIG. 1B]
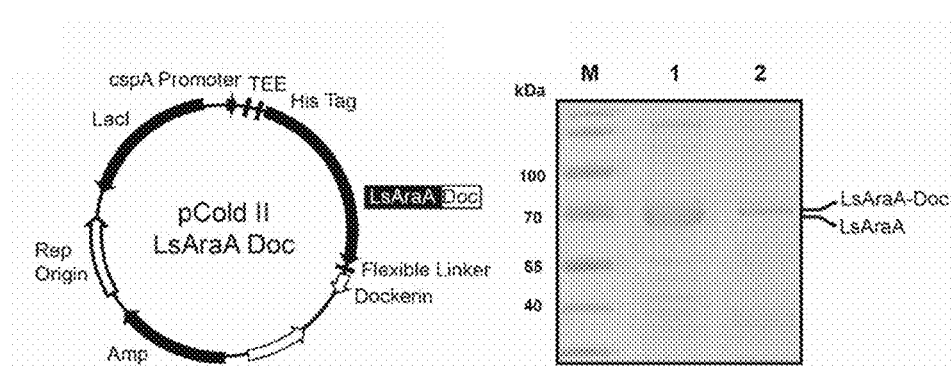
[FIG. 2]
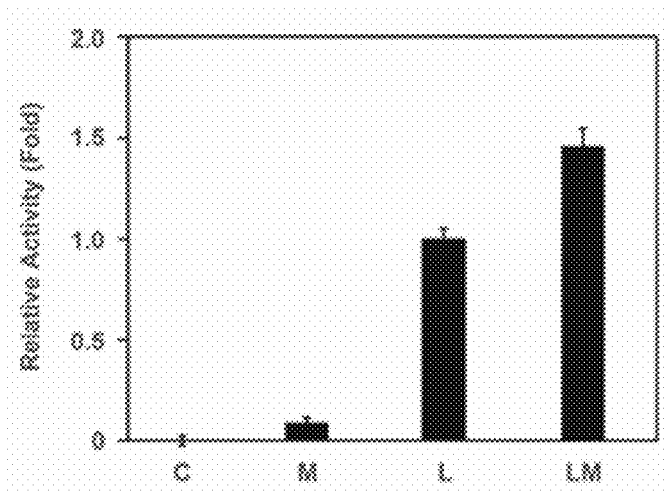

[FIG. 3]
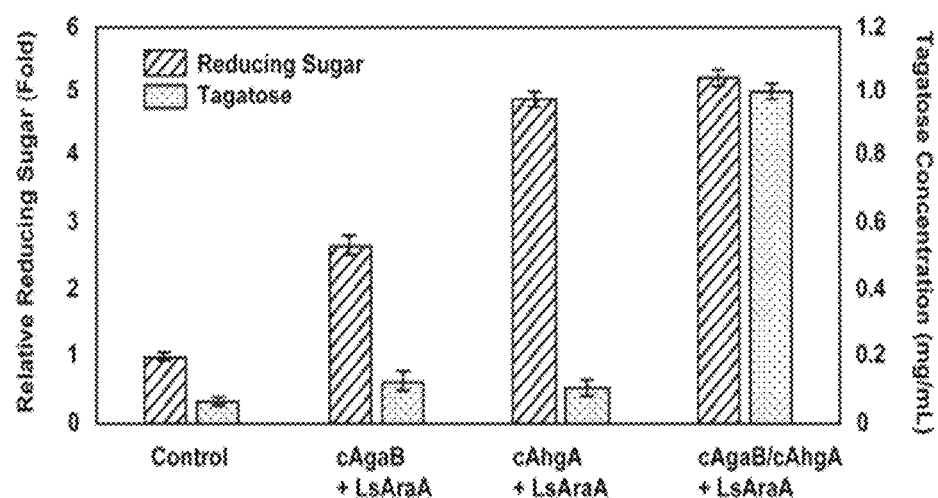

[FIG. 4A]
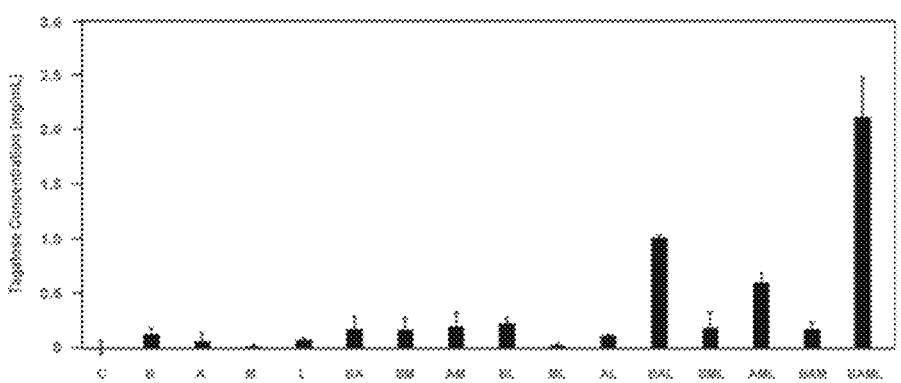
[FIG. 4B]
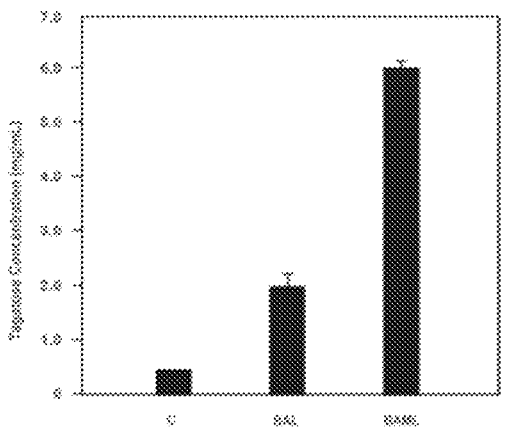

SEQUENCE LISTING

```
<160> NUMBER OF SEQ ID NOS: 36

<210> SEQ ID NO 1
<211> LENGTH: 492
<212> TYPE: PRT
<213> ORGANISM: Lactobacillus casei

<400> SEQUENCE: 1

Ser Leu Ser Ala Arg Val Ser Phe Lys Lys His Val Lys Lys Gly Val
1               5                   10                  15

Phe Ile Met Leu Asn Thr Glu Asn Tyr Glu Phe Trp Phe Val Thr Gly
            20                  25                  30

Ser Gln Ser Leu Tyr Gly Glu Glu Thr Leu Arg Ser Val Glu Lys Asp
        35                  40                  45

Ala Lys Glu Ile Val Glu Lys Leu Asn Ala Ser Arg Gln Leu Pro Tyr
    50                  55                  60

Pro Ile Val Phe Lys Leu Val Ala Thr Ala Asp Asn Ile Thr Lys
65                  70                  75                  80

Val Met Lys Glu Ala Asn Tyr Asn Asp His Val Ala Gly Val Ile Thr
            85                  90                  95

Trp Met His Thr Phe Ser Pro Ala Lys Asn Trp Ile Arg Gly Thr Lys
            100                 105                 110

Leu Leu Gln Lys Pro Leu Leu His Leu Ala Thr Gln Phe Leu Asn Lys
        115                 120                 125

Ile Pro Tyr Asp Thr Ile Asp Phe Asp Tyr Met Asn Leu Asn Gln Ser
    130                 135                 140

Ala His Gly Asp Arg Glu Tyr Ala Phe Ile Asn Ala Arg Leu Arg Lys
145                 150                 155                 160

Asn Asn Lys Ile Ile Ser Gly Tyr Trp Gly Asp Glu Asp Val Gln Lys
                165                 170                 175

Ala Met Ala Lys Trp Met Asp Val Ala Val Ala Tyr Asn Glu Ser Phe
            180                 185                 190

Lys Ile Lys Val Val Thr Phe Ala Asp Lys Met Arg Asn Val Ala Val
        195                 200                 205

Thr Asp Gly Asp Lys Val Glu Ala Gln Ile Lys Phe Gly Trp Thr Val
    210                 215                 220

Asp Tyr Trp Gly Val Gly Asp Leu Val Ala Glu Val Asn Ala Val Ser
225                 230                 235                 240

Glu Ala Asp Ile Asp Ala Lys Tyr Ala Asp Leu Gln Lys Glu Tyr Asp
                245                 250                 255

Phe Val Glu Gly Gln Asn Thr Pro Glu Lys Phe Glu His Asn Val Lys
            260                 265                 270

Tyr Gln Ile Arg Glu Tyr Phe Gly Leu Lys Lys Phe Met Asp Asp Arg
        275                 280                 285
```

Gly Tyr Thr Ala Phe Thr Thr Asn Phe Glu Asp Leu Val Gly Leu Glu
        290                 295                 300

Gln Leu Pro Gly Leu Ala Ala Gln Leu Leu Met Ala Glu Gly Tyr Gly
305                 310                 315                 320

Phe Ala Gly Glu Gly Asp Trp Lys Thr Ala Ala Leu Asp Arg Leu Leu
                325                 330                 335

Lys Ile Met Ala His Asn Glu Lys Thr Val Phe Met Glu Asp Tyr Thr
                340                 345                 350

Leu Asp Leu Arg Gln Gly His Glu Ala Ile Leu Gly Ser His Met Leu
            355                 360                 365

Glu Val Asp Pro Ser Ile Ala Ser Asp Lys Pro Arg Val Glu Val His
        370                 375                 380

Pro Leu Asp Ile Gly Asp Lys Asp Pro Ala Arg Leu Val Phe Thr
385                 390                 395                 400

Gly Met Gln Gly Asp Ala Val Asp Val Thr Met Ala Asp Tyr Gly Asp
                405                 410                 415

Glu Phe Lys Leu Met Ser Tyr Asp Val Arg Gly Asn Lys Pro Glu Ala
                420                 425                 430

Asp Thr Pro His Leu Pro Val Ala Lys Gln Leu Trp Thr Pro Lys Gln
            435                 440                 445

Gly Leu Arg Glu Gly Ala Val Gly Trp Leu Thr Val Gly Gly Gly His
        450                 455                 460

His Thr Val Leu Ser Phe Ala Val Asp Ser Glu Gln Leu Gln Asp Leu
465                 470                 475                 480

Ser His Leu Phe Asp Leu Thr Tyr Val Asn Ile Lys
                485                 490

<210> SEQ ID NO 2
<211> LENGTH: 29
<212> TYPE: DNA
<213> ORGANISM: Artificial Sequence
<220> FEATURE:
<223> OTHER INFORMATION: LsAraA Sac I FORWARD PRIMER

<400> SEQUENCE: 2
gcgcgagctc ctcgttaagc gcaagagtc                                     29

<210> SEQ ID NO 3
<211> LENGTH: 29
<212> TYPE: DNA
<213> ORGANISM: Artificial Sequence
<220> FEATURE:
<223> OTHER INFORMATION: LsAraA Hind III REWARD PRIMER

<400> SEQUENCE: 3
gcgcgagctc ctcgttaagc gcaagagtc                                     29

<210> SEQ ID NO 4
<211> LENGTH: 1479
<212> TYPE: DNA
<213> ORGANISM: Artificial Sequence
<220> FEATURE:
<223> OTHER INFORMATION: Lactobacillus Arabinose Isomerase

<400> SEQUENCE: 4
tcgttaagcg caagagtcag tttcaaaaag cacgttaaaa aaggagtctt tatcatgtta      60
aacacagaaa attatgaatt tggtttgtc acagggagtc aatcattata cggcgaagaa     120
accctccgat cagttgaaaa agacgctaag gaaatcgttg aaaaattaaa tgcgagtcgc     180

```
caattacctt acccaatcgt tttcaaatta gtcgcaacaa ctgctgataa tattacgaaa      240
gtgatgaaag aagctaacta caacgatcac gttgctggtg tgatcacttg gatgcatact      300
ttctcacctg ctaaaaactg gatccgcggg acaaaattat tacaaaaacc attacttcat      360
ttagcaaccc aattcttaaa caagattcca tacgacacaa tcgatttcga ttacatgaac      420
ttaaaccaat cagctcatgg tgatcgcgaa tatgccttca tcaatgcgcg tttacgtaaa      480
aataacaaga ttatctcagg ttactggggt gatgaagacg ttcaaaaagc aatggctaaa      540
tggatggacg ttgcggtagc ttacaacgaa tcattcaaga ttaaagtcgt gacatttgct      600
gataaaatgc ggaacgtggc cgtcacagac ggtgataaag tcgaagctca aatcaaattt      660
ggttggacgg ttgattattg gggtgtcggt gatttagtcg cagaagtcaa tgctgtctca      720
gaggctgata ttgatgctaa gtatgctgat ttacaaaaag aatacgactt tgttgaaggt      780
caaaatacac ctgaaaaatt cgaacacaat gttaaatacc aaattcgtga atacttcggt      840
ttgaagaaat ttatggacga tcgtggctac acagccttca caaccaactt cgaagattta      900
gttgggttgg aacaattacc tggtttagca gcccaattat tgatggctga aggttatggt      960
ttcgccggtg aaggggactg gaagacagct gctttagatc gcttgttgaa gattatggct     1020
cataatgaaa agacggtctt catggaagat tacacacttg atttacgtca aggccacgaa     1080
gctatcttgg ggtcacatat gcttgaagtt gatccttcaa tcgcgtcaga taaaccacgg     1140
gttgaagttc acccattaga tatcggcgat aaagacgatc ctgcacgttt agtcttcaca     1200
gggatgcaag gcgatgctgt ggacgtcaca atggctgatt atggcgacga attcaaattg     1260
atgtcatatg atgttcgcgg caacaaacca gaagccgata caccacactt gccagttgct     1320
aaacaactct ggacaccaaa acaaggctta cgcgaaggtg ccgttggttg gttaaccgtt     1380
ggtggtggtc accatacagt cttatcattt gctgttgatt cagaacaatt acaagattta     1440
agtcacttgt ttgatttaac ttacgtcaat attaaataa                             1479
```

<210> SEQ ID NO 5
<211> LENGTH: 29
<212> TYPE: DNA
<213> ORGANISM: Artificial Sequence
<220> FEATURE:
<223> OTHER INFORMATION: LsAraA Sac I forward primer

<400> SEQUENCE: 5
gcgcgagctc ctcgttaagc gcaagagtc                                         29

<210> SEQ ID NO 6
<211> LENGTH: 38
<212> TYPE: DNA
<213> ORGANISM: Artificial Sequence
<220> FEATURE:
<223> OTHER INFORMATION: Dockerin Sac I reward primer

<400> SEQUENCE: 6
cagcggatcc tttaatattg acgtaagtta aatcaaac                               38

<210> SEQ ID NO 7
<211> LENGTH: 25
<212> TYPE: DNA
<213> ORGANISM: Artificial Sequence
<220> FEATURE:
<223> OTHER INFORMATION: Arabinose Isomerase c-terminal forward primer

<400> SEQUENCE: 7
caatattaaa ggatccgctg gctcc                                          25

<210> SEQ ID NO 8
<211> LENGTH: 35
<212> TYPE: DNA
<213> ORGANISM: Artificial Sequence
<220> FEATURE:
<223> OTHER INFORMATION: Arabinose Isomerase Kpn I reward primer

<400> SEQUENCE: 8
ggtaccttat aaaagcattt ttttaagaac agcta                               35

<210> SEQ ID NO 9
<211> LENGTH: 10
<212> TYPE: DNA
<213> ORGANISM: Artificial Sequence
<220> FEATURE:
<223> OTHER INFORMATION: Endo-beta-1,4-glucanase-B N-terminal

<400> SEQUENCE: 9
ggatccgctg                                                           10

<210> SEQ ID NO 10
<211> LENGTH: 10
<212> TYPE: DNA
<213> ORGANISM: Artificial Sequence
<220> FEATURE:
<223> OTHER INFORMATION: Endo-beta-1,4-glucanase-B C-terminal

<400> SEQUENCE: 10
caatattaaa                                                           10

<210> SEQ ID NO 11
<211> LENGTH: 195
<212> TYPE: DNA
<213> ORGANISM: Clostridium cellulovorans

<400> SEQUENCE: 11
ggatccgctg gctccgctgc tggttctggg gaattcgatg ttaacaaaga tggaaaggta    60
aatgctatcg attatgcagt gcttaaatca attcttttag gtacaaatac taacgttgat   120
ttatcagtat cagacatgaa taaggatggt aaagtaaatg ctttggattt agctgttctt   180
aaaaaaatgc tttta                                                    195

<210> SEQ ID NO 12
<211> LENGTH: 29
<212> TYPE: DNA
<213> ORGANISM: Artificial Sequence
<220> FEATURE:
<223> OTHER INFORMATION: LsAraA-Dockerin Sac I Forward primer

<400> SEQUENCE: 12
gcgcgagctc ctcgttaagc gcaagagtc                                      29

<210> SEQ ID NO 13
<211> LENGTH: 35
<212> TYPE: DNA
<213> ORGANISM: Artificial Sequence
<220> FEATURE:
<223> OTHER INFORMATION: LsAraA-Dockerin Kpn I Reward primer

<400> SEQUENCE: 13
ggtaccttat aaaagcattt ttttaagaac agcta                               35

<210> SEQ ID NO 14
<211> LENGTH: 1686
<212> TYPE: DNA
<213> ORGANISM: Artificial Sequence
<220> FEATURE:
<223> OTHER INFORMATION: LsAraA-Dockerin

<400> SEQUENCE: 14

```
gagctctcgt taagcgcaag agtcagtttc aaaaagcacg ttaaaaaagg agtctttatc      60
atgttaaaca cagaaaatta tgaattttgg tttgtcacag ggagtcaatc attatacggc     120
gaagaaaccc tccgatcagt tgaaaagac gctaaggaaa tcgttgaaaa attaaatgcg     180
agtcgccaat taccttaccc aatcgttttc aaattagtcg caacaactgc tgataatatt     240
acgaaagtga tgaaagaagc taactacaac gatcacgttg ctggtgtgat cacttggatg     300
catactttct cacctgctaa aaactggatc cgcgggacaa aattattaca aaaccatta     360
cttcatttag caacccaatt cttaaacaag attccatacg acacaatcga tttcgattac     420
atgaacttaa accaatcagc tcatggtgat cgcgaatatg ccttcatcaa tgcgcgttta     480
cgtaaaaata caagattat ctcaggttac tggggtgatg aagacgttca aaaagcaatg     540
gctaaatgga tggacgttgc ggtagcttac aacgaatcat tcaagattaa agtcgtgaca     600
tttgctgata aaatgcggaa cgtggccgtc acagacggtg ataaagtcga agctcaaatc     660
aaatttggtt ggacggttga ttattgggggt gtcggtgatt tagtcgcaga agtcaatgct     720
gtctcagagg ctgatattga tgctaagtat gctgatttac aaaaagaata cgactttgtt     780
gaaggtcaaa atacacctga aaaattcgaa cacaatgtta ataccaaat cgtgaatac     840
ttcggtttga agaaatttat ggacgatcgt ggctacacag ccttcacaac caacttcgaa     900
gattagttg gttggaaca attacctggt ttagcagccc aattattgat ggctgaaggt     960
tatggtttcg ccggtgaagg ggactggaag acagctgctt tagatcgctt gttgaagatt    1020
atggctcata tgaaaagac ggtcttcatg gaagattaca cacttgattt acgtcaaggc    1080
cacgaagcta tcttgggggtc acatatgctt gaagttgatc cttcaatcgc gtcagataaa    1140
ccacggggttg aagttcaccc attagatatc ggcgataaag acgatcctgc acgtttagtc    1200
ttcacaggga tgcaaggcga tgctgtggac gtcacaatgg ctgattatgg cgacgaattc    1260
aaattgatgt catatgatgt tcgcggcaac aaaccagaag ccgatacacc acacttgcca    1320
gttgctaaac aactctggac accaaaacaa ggcttacgcg aaggtgccgt tggttggtta    1380
accgttggtg gtggtcacca tacagtctta tcatttgctg ttgattcaga acaattacaa    1440
gatttaagtc acttgtttga tttaacttac gtcaatatta aaggatccgc tggctccgct    1500
gctggttctg gggaattcga tgttaacaaa gatggaaagg taaatgctat cgattatgca    1560
gtgcttaaat caattctttt aggtacaaat actaacgttg atttatcagt atcagacatg    1620
aataaggatg gtaaagtaaa tgctttggat ttagctgttc ttaaaaaaat gctttttataa    1680
ggtacc                                                               1686
```

<210> SEQ ID NO 15
<211> LENGTH: 22
<212> TYPE: DNA
<213> ORGANISM: Artificial Sequence
<220> FEATURE:
<223> OTHER INFORMATION: Mini-CelluloseBinding protein A Forward primer

<400> SEQUENCE: 15

```
ggatccgcag cgacatcatc aa                                               22
```

<210> SEQ ID NO 16
<211> LENGTH: 33
<212> TYPE: DNA
<213> ORGANISM: Artificial Sequence
<220> FEATURE:
<223> OTHER INFORMATION: Mini-CelluloseBinding protein A Reward primer

<400> SEQUENCE: 16
gcgcctcgag gctataggat ctccaatatt tat                           33

<210> SEQ ID NO 17
<211> LENGTH: 1647
<212> TYPE: DNA
<213> ORGANISM: Artificial Sequence
<220> FEATURE:
<223> OTHER INFORMATION: Clostridium cellulovorans CelluloseBinding
      protein gene mCbpA

<400> SEQUENCE: 17
gcagcgacat catcaatgtc agttgaattt tacaactcta acaaatcagc acaaacaaac    60
tcaattacac caataatcaa aattactaac acatctgaca gtgatttaaa tttaaatgac   120
gtaaaagtta gatattatta cacaagtgat ggtacacaag acaaactttt ctggtgtgac   180
catgctggtg cattattagg aaatagctat gttgataaca ctagcaaagt gacagcaaac   240
ttcgttaaag aaacagcaag cccaacatca acctatgata catatgttga atttggattt   300
gcaagcggag cagctactct taaaaaagga caatttataa ctattcaagg aagaataaca   360
aaatcagact ggtcaaacta cactcaaaca atgactatt catttgatgc aagtagttca   420
acaccagttg taaatccaaa agttacagga tatataggtg gagctaaagt acttggtaca   480
gcaccaggtc cagatgtacc atcttcaata attaatccta cttctgcaac atttgataaa   540
aatgtaacta acaagcaga tgttaaaact actatgactt taaatggtaa cacatttaaa   600
acaattacag atgcaaacgg tacagctcta aatgcaagca ctgattatag tgtttctgga   660
aatgatgtaa caataagcaa agcttattta gcaaaacaat cagtaggaac aactacatta   720
aactttaact ttagtgcagg aaatcctcaa aaattagtaa ttacagtagt tgacacacca   780
gttgaagctg taacagctac aattggaaaa gtacaagtaa atgctggaga aacggtagca   840
gtaccagtta acttaacaaa agttccagcg ctggtttag caacaattga attaccatta   900
acttttgatt ctgcatcatt agaagtagta tcaataactg ctggagatat cgtattaaat   960
ccatcagtaa acttctcttc tacagtaagt ggaagcacaa taaaattatt attcttagat  1020
gatacattag gaagccaatt aatcactaag gatggagttt ttgcaacaat aacatttaaa  1080
gcaaaagcta taactggaac aactgcaaaa gtaacttcag ttaaattagc tggaacacca  1140
gtagttggtg atgcgcaatt acaagaaaaa ccttgtgcag ttaacccagg aacagtaact  1200
atcaatccaa tcgataatag aatgcaaatt tcagttggaa cagcaacagt aaaagctgga  1260
gaaatagcag cagtgccagt aacattaaca agtgttccat caactggaat agcaactgct  1320
gaagcacaag taagttttga tgcaacatta ttagaagtag catcagtaac tgctggagat  1380
atcgtattaa atccaacagt aaacttctct tatacagtaa acggaaatgt aataaaatta  1440
ttattcctag atgatacatt aggaagccaa ttaattagta aagatggagt tttgtaaca  1500 ataaacttca agcaaaagc tgtaacaagc acagtaacaa caccagttac agtatcagga  1560
acacctgtat ttgcagatgg tacattagca gaagtacaat ctaaaacagc agcaggtagc  1620
gttacaataa atattggaga tcctata                                     1647

<210> SEQ ID NO 18
<211> LENGTH: 33
<212> TYPE: DNA
<213> ORGANISM: Artificial Sequence
<220> FEATURE:
<223> OTHER INFORMATION: Beta-Agarase AgaB Sac I Forward primer

<400> SEQUENCE: 18
gcgcgagctc cggcgacaat tcaaaatttg ata                                    33

<210> SEQ ID NO 19
<211> LENGTH: 32
<212> TYPE: DNA
<213> ORGANISM: Artificial Sequence
<220> FEATURE:
<223> OTHER INFORMATION: Beta-Agarase AgaB Reward primer

<400> SEQUENCE: 19
cagcggatcc tttctctaca ggtttataga tc                                     32

<210> SEQ ID NO 20
<211> LENGTH: 1005
<212> TYPE: DNA
<213> ORGANISM: Artificial Sequence
<220> FEATURE:
<223> OTHER INFORMATION: Beta-Agarase

<400> SEQUENCE: 20
ggcgacaatt caaaatttga tagtgcaacg gatttgccgg ttgaacaaga acaagaacag        60
gaaacggaac aagagggaga acccgaagaa agttcggagc aagaccttgt cgaggaggtc       120
gattggaagg atattcccgt acccgccgat gcaggaccga atatgaagtg ggagtttcaa       180
gagatttccg ataattttga atatgaggcc cctgcggata taaggggag tgaatttctc       240 gaaaagtggg acgattttta tcacaatgcc tgggcaggcc cagggctgac cgaatggaaa       300
cgggacaggt cctatgtagc cgatggcgag ctaaagatgt gggcgacaag aaaaccgggc       360
tccgataaaa taaacatggg gtgcattact tctaagaccc gagtggtcta tcctgtttat       420
attgaagcaa gggcaaaggt catgaactct accttggctt cggatgtttg gctcttaagt       480
gccgatgaca cccaagagat agatattcta gaggcatatg gggccgatta ttccgaaagt       540
gccgaaaagg atcattccta tttttctaaa aaggtacaca taagccatca cgtctttatt       600
cgagacccat ttcaagatta tcaaccaaag gatgccggtt cttggttcga agacggcacc       660
gtctggaaca aagagttcca taggtttggt gtgtattgga gggatccatg gcatctagaa       720
tattacatag acggtgttct ggtgaggacc gtttcgggaa aggacattat cgaccccaaa       780
cactttacga atacaacgga tcccggtaat acggaaatcg ataccgcac cggtctcaat       840 aaagaaatgg atattattat caatacagaa gaccaaactt ggcggtcttc accggcctcg       900
ggtttacagt ctaataccta tacgccaacg gacaatgaat tgagcaatat agaaaacaat       960
acgttcgggg tcgattggat caggatctat aaacctgtag agaaa                      1005

<210> SEQ ID NO 21
<211> LENGTH: 26
<212> TYPE: DNA
<213> ORGANISM: Artificial Sequence
<220> FEATURE:
<223> OTHER INFORMATION: Beta-Agarase AgaB C-terminal Forward primer

<400> SEQUENCE: 21
tgtagagaaa ggatccgctg gctccg                                            26

<210> SEQ ID NO 22
<211> LENGTH: 49
<212> TYPE: DNA
<213> ORGANISM: Artificial Sequence
<220> FEATURE:
<223> OTHER INFORMATION: Beta-Agarase AgaB Not I Reward primer

<400> SEQUENCE: 22
gcgcggccgc tcaatgatga tgatgatgat gtaaaagcat tttttttaag       49

<210> SEQ ID NO 23
<211> LENGTH: 195
<212> TYPE: DNA
<213> ORGANISM: Artificial Sequence
<220> FEATURE:
<223> OTHER INFORMATION: Dockerin of Endo-beta-1,4-glucanase-B

<400> SEQUENCE: 23
ggatccgctg gctccgctgc tggttctggg gaattcgatg ttaacaaaga tggaaaggta       60
aatgctatcg attatgcagt gcttaaatca attcttttag gtacaaatac taacgttgat      120
ttatcagtat cagacatgaa taaggatggt aaagtaaatg ctttggattt agctgttctt      180
aaaaaaatgc tttta                                                      195

<210> SEQ ID NO 24
<211> LENGTH: 33
<212> TYPE: DNA
<213> ORGANISM: Artificial Sequence
<220> FEATURE:
<223> OTHER INFORMATION: AgaB-Dockerin Sac I Forward Primer

<400> SEQUENCE: 24
gcgcgagctc cggcgacaat tcaaaatttg ata       33

<210> SEQ ID NO 25
<211> LENGTH: 49
<212> TYPE: DNA
<213> ORGANISM: Artificial Sequence
<220> FEATURE:
<223> OTHER INFORMATION: AgaB-Dockerin Not I Reward Primer

<400> SEQUENCE: 25
gcgcggccgc tcaatgatga tgatgatgat gtaaaagcat tttttttaag       49

<210> SEQ ID NO 26
<211> LENGTH: 159
<212> TYPE: DNA
<213> ORGANISM: Artificial Sequence
<220> FEATURE:
<223> OTHER INFORMATION: Chimeric Beta-Agarase AgaB

<400> SEQUENCE: 26
gatgttaaca aagatggaaa ggtaaatgct atcgattatg cagtgcttaa atcaattctt       60
ttaggtacaa atactaacgt tgatttatca gtatcagaca tgaataagga tggtaaagta      120
aatgctttgg atttagctgt tcttaaaaaa atgctttta                            159

<210> SEQ ID NO 27
<211> LENGTH: 32
<212> TYPE: DNA
<213> ORGANISM: Artificial Sequence
<220> FEATURE:
<223> OTHER INFORMATION: 3,6-Anhydro-L-Galactosidase EcoR I Forward
      primer

<400> SEQUENCE: 27
gcgcgaattc gatgaacaaa tactcccaat tt                          32

<210> SEQ ID NO 28
<211> LENGTH: 30
<212> TYPE: DNA
<213> ORGANISM: Artificial Sequence
<220> FEATURE:
<223> OTHER INFORMATION: Endo-beta-1,4-glucanase-B N-terminal Reward
      primer

<400> SEQUENCE: 28
cagcggatcc ttgttttttt actcctttag                             30

<210> SEQ ID NO 29
<211> LENGTH: 1224
<212> TYPE: DNA
<213> ORGANISM: Artificial Sequence
<220> FEATURE:
<223> OTHER INFORMATION: 3,6-Anhydro-L-Galactosidase

<400> SEQUENCE: 29
atgaacaaat actcccaatt tttaattttt gctgcggtgc tggtatcggc ctgcaattct     60
cccaaaacta caaagaaat gaaatctaca gatgattgcc cagagaaggt gacgtttact    120
cccgaacaaa ttgaccatct cggcattacg ataccaacc atttgagcgc tgcgtcaaaa    180
agagccttga atggcctac ggacttgggt aatgaatggt ttattcaatt tggtccgtta    240
caacctttaa aggggattt ggcttatgag aaggtgtcg ttcgtcgtga tccaagtgcc    300
ataatcaaag agaatggaaa gtactacgtg tggtattcta aaagtaccgg ccaacgcaa    360 ggttttggtg gggatattga aaagataag gttttccgt gggatcgatg tgatatttgg    420
tatgctacct ccgaagatgg ttggacgtgg aagaagaag gtcccgcagt aacaagaggt    480 gaaaagggg cttatgatga tcgctccgtt tttaccgttg agatcatgaa atgggaagat    540
aagtactacc tctgctatca aacggtaaaa tcaccctata atgtccgtgt taaaaatcaa    600
gtaggtctgg cttgggcgga ttctcccgac gggccatgga ccaaaagtga agagcctatt    660
ttgagtcctg ccgataacgg agtgtggaag ggtgaagagc aagatcgttt cgccgtgatt    720
aaaaaaggtg attttgatag ccataaagta catgatccat gtattatacc ttataagggg    780
aaattctatc tctattacaa aggggaacag atgggtgaag cgattacttt cggcggaaga    840
cagatacgtc atggtgtggc catagccgac aatcccaaag gccttacgt gaaatctcca    900 tataacccta ttagcaatag tggtcatgaa atctgtgttt ggccttataa cggaggtatt    960
gcttcgttga tcactacaga tggtcctgaa aagaatacga tccagtgggc tccagacgga   1020
attaactttg aaattaaatc ggtaatacca ggggtcaatg cccatgctat cggactgaac   1080
cgaacagcgg atgttgaaaa ggaaccgacc gaaatttac gatggggatt gacgcatata   1140
tacaataatg gcgattacca gagtatcatg cgttttttctt cggaaagaaa aacacgtcac   1200
gtagctaaag gagtaaaaaa acaa                                         1224

<210> SEQ ID NO 30
<211> LENGTH: 26
<212> TYPE: DNA
<213> ORGANISM: Artificial Sequence
<220> FEATURE:
<223> OTHER INFORMATION: Endo-beta-1,4-Glucanase-B Forward primer

<400> SEQUENCE: 30

```
aaaaaaacaa ggatccgctg gctccg                                          26
```

<210> SEQ ID NO 31
<211> LENGTH: 36
<212> TYPE: DNA
<213> ORGANISM: Artificial Sequence
<220> FEATURE:
<223> OTHER INFORMATION: Endo-beta-1,4-Glucanase-B Hind III Reward
      primer

<400> SEQUENCE: 31

```
gcgcaagctt taaaagcatt tttttaagaa cagcta                                36
```

<210> SEQ ID NO 32
<211> LENGTH: 195
<212> TYPE: DNA
<213> ORGANISM: Artificial Sequence
<220> FEATURE:
<223> OTHER INFORMATION: Dockerin of Endo-beta-1,4-Glucanase-B

<400> SEQUENCE: 32

```
ggatccgctg gctccgctgc tggttctggg gaattcgatg ttaacaaaga tggaaaggta     60
aatgctatcg attatgcagt gcttaaatca attcttttag gtacaaatac taacgttgat    120
ttatcagtat cagacatgaa taaggatggt aaagtaaatg ctttggattt agctgttctt    180
aaaaaaatgc tttta                                                     195
```

<210> SEQ ID NO 33
<211> LENGTH: 32
<212> TYPE: DNA
<213> ORGANISM: Artificial Sequence
<220> FEATURE:
<223> OTHER INFORMATION: 3,6-Anhydro-L-Galactosidase linked Dockerin
      EcoR I Forward primer

<400> SEQUENCE: 33

```
gcgcgaattc gatgaacaaa tactcccaat tt                                   32
```

<210> SEQ ID NO 34
<211> LENGTH: 36
<212> TYPE: DNA
<213> ORGANISM: Artificial Sequence
<220> FEATURE:
<223> OTHER INFORMATION: 3,6-Anhydro-L-Galactosidase linked Dockerin
      Hind III Reward primer

<400> SEQUENCE: 34

```
gcgcaagctt taaaagcatt tttttaagaa cagcta                                36
```

<210> SEQ ID NO 35
<211> LENGTH: 159
<212> TYPE: DNA
<213> ORGANISM: Artificial Sequence
<220> FEATURE:
<223> OTHER INFORMATION: Chimeric Dockerin

<400> SEQUENCE: 35

```
gatgttaaca aagatggaaa ggtaaatgct atcgattatg cagtgcttaa atcaattctt     60
ttaggtacaa atactaacgt tgatttatca gtatcagaca tgaataagga tggtaaagta    120
aatgctttgg atttagctgt tcttaaaaaa atgctttta                           159
```

<210> SEQ ID NO 36
<211> LENGTH: 1224

```
<212> TYPE: DNA
<213> ORGANISM: Artificial Sequence
<220> FEATURE:
<223> OTHER INFORMATION: Chimeric 3,6-Anhydro-L-Galactosidase

<400> SEQUENCE: 36
atgaacaaat actcccaatt tttaattttt gctgcggtgc tggtatcggc ctgcaattct      60
cccaaaacta caaaagaaat gaaatctaca gatgattgcc cagagaaggt gacgtttact     120
cccgaacaaa ttgaccatct cggcattacg gataccaacc atttgagcgc tgcgtcaaaa     180
agagccttga aatggcctac ggacttgggt aatgaatggt ttattcaatt tggtccgtta     240
caacctttaa aggggpattt ggcttatgag gaaggtgtcg ttcgtcgtga tccaagtgcc     300
ataatcaaag agaatggaaa gtactacgtg tggtattcta aaagtaccgg gccaacgcaa     360
ggttttggtg gggatattga aaaagataag gttttccgt gggatcgatg tgatatttgg      420
tatgctacct ccgaagatgg ttggacgtgg aaagaagaag gtcccgcagt aacaagaggt     480
gaaaaagggg cttatgatga tcgctccgtt tttaccgttg agatcatgaa atgggaagat     540
aagtactacc tctgctatca aacggtaaaa tcaccctata atgtccgtgt taaaaatcaa     600
gtaggtctgg cttgggcgga ttctcccgac gggccatgga ccaaaagtga agagcctatt     660
ttgagtcctg ccgataacgg agtgtggaag ggtgaagagc aagatcgttt cgccgtgatt     720
aaaaaaggtg attttgatag ccataaagta catgatccat gtattatacc ttataagggg     780
aaattctatc tctattacaa aggggaacag atgggtgaag cgattacttt cggcggaaga     840
cagatacgtc atggtgtggc catagccgac aatcccaaag gccttacgt gaaatctcca      900 tataaccctta ttagcaatag tggtcatgaa atctgtgttt ggccttataa cggaggtatt     960
gcttcgttga tcactacaga tggtcctgaa aagaatacga tccagtgggc tccagacgga    1020
attaactttg aaattaaatc ggtaatacca ggggtcaatg cccatgctat cggactgaac    1080
cgaacagcgg atgttgaaaa ggaaccgacc gaaattttac gatggggatt gacgcatata    1140
tacaataatg gcgattacca gagtatcatg cgttttttctt cggaaagaaa aacacgtcac    1200
gtagctaaag gagtaaaaaa acaa                                            1224
```

AGARASE-3,6-ANHYDRO-L-GALACTOSIDASE-ARABINOSE ISOMERASE ENZYME COMPLEX AND METHOD FOR PRODUCTION OF TAGATOSE FROM AGAR USING THE SAME

CROSS-REFERENCE TO RELATED APPLICATION

This application claims the benefit under 35 USC 119(a) of Korean Patent Application No. 10-2019-0019901 filed on Feb. 20, 2019, in the Korean Intellectual Property Office, the entire disclosures of which are incorporated herein by reference for all purposes.

TECHNICAL FIELD

The present disclosure relates to an agarase-3,6-anhydro-L-galactosidase-arabinose isomerase enzyme complex and a method for producing tagatose from agar using the same. More particularly, the present disclosure relates to a method for preparing tagatose using agarooligosaccharide present in marine biomass (agar). It relates to an agarase complex consisting of agarase, 3,6-anhydro-L-galactosidase and arabinose isomerase, and a method for degrading agar and producing tagatose using the same.

BACKGROUND ART

Recently, marine algae having cell walls consisting of many fibrils and various polysaccharides is drawing attentions as a new raw material of bioenergy. Marine algae is advantageous in that the pretreatment process can be simplified due to low (hardly soluble) lignin content. In addition, the marine algae is composed of about 60-95% of water and other components about 50% of which are carbohydrates. The carbohydrates can be converted to monosaccharides for producing bioenergy and biochemicals.

In Korea and Japan, the red algae layer (mostly *Porphyra yezoensis*) is cultivated actively. Red algae accounts for more than half of the marine algae growing wild in Korea. The red algae that may be used in the present disclosure is agar. Agar is the most diverse species of red algae with superior productivity. Agar consists of about 50-70% of galactan, which is the main ingredient, as well as about 15-25% of cellulose, less than 15% or proteins and less than 7% of lipids.

If agar, which is the representative byproduct in processing and extraction of red algae, is degraded effectively, galactose or glucose useful for ethanol production can be obtained. In addition, the metabolites such as dioses, trioses, oligosaccharides, etc. produced during the degradation can be useful physiologically active substances. At present, seaweed polysaccharides such as agar and carrageenan are extracted from red algae through treatment with alkalis, acids, enzymes, etc. and are usefully used industrially as food or cosmetic additives or healthful food resources. However, because red algae has a complicated structure difficult to be degraded, there is difficulty in using it as a substrate for biofuel production. Also, there are problems in disposing of byproducts and wastes. Agarase, which is an enzyme that degrades agar, hydrolyzes β-1,4 linkages in agarose and produces neoagarooligosaccharides with galactose disaccharide or trisaccharide residues. κ-Carrageenase, which is an enzyme that degrades κ-carrageenan, breaks down the 3-,4-linkage galactose units of κ-carrageenan to produce disaccharide carrageenan residues. Agarase can be classified into α-agarase and β-agarase based on the linkage degraded by the enzyme. The α-agarase degrades the α-1,3 linkages in the galactose residues in agarose to produce agarooligosaccharides. The agarooligosaccharides are reported to have apoptosis-inducing activity, anticancer activity, antiviral activity, antioxidant activity, immuno-modulatory activity, antiallergic activity, antiinflammatory activity, etc. And, the β-agarase degrades the β-1,4 linkages in the galactose residues in agarose to produce neoagarooligosaccharides. The neoagarooligosaccharides are reported to inhibit bacterial growth and have antioxidant activity, starch aging-inhibiting effect, skin-moisturizing effect, skin-whitening effect, etc.

Cellulose is one of the most abundant biomass in nature. The enzymes that degrade cellulose are produced by fibrous fungi or several bacteria. Among them, anaerobic bacteria in the class Clostridia produce enzyme complexes using domains called cohesion and dockerin. Since the enzyme complex has several cohesin domains in the scaffold protein, binding is possible with enzymes having dockerin domains. Also, the scaffold protein has a carbohydrate-binding module (CBM), which improves the efficiency of complex formation. An enzyme having the dockerin domain and capable of forming an enzyme complex is called a chimeric enzyme. By using an enzyme having a dockerin domain engineered to bind a specific cohesin domain, a complex can be formed as desired by selecting the necessary enzyme. The formed enzyme complex degrades a polysaccharide into smaller polysaccharide units, which are degraded further into smaller disaccharides or monosaccharides by the next enzyme.

Tagatose is a rare sugar contained in trace amounts in dairy products or some plants, and is used in diet food products as a low-calorie sweetener. Generally, D-tagatose is an isomer of galactose and a C4 epimer of D-fructose. It is a low-calorie sweetener which is 92% as sweet as table sugar, but with only about 30% of the calories (1.5 kcal/g). Additionally, it is a non-caloric sweetener which is hardly metabolized during the in-vivo absorption process. 15-20% of the amount of tagatose ingested is absorbed into the body, but this absorption does not affect the blood glucose level because it is due to decomposition by microorganisms in the large intestine not by human's own digestive capability. Accordingly, it is expected to provide a blood glucose level-controlling effect for diabetic patients, and is known to provide food for enteric microorganisms, thereby helping excretion. Tagatose is a healthful sweetener that can be safely included in chocolate, gums, bread, candies, etc. favored by children, instead of sugar, because it does not cause tooth decay. Therefore, it is drawing a lot of attentions as a substance that can contribute to the prevention of diseases caused by excessive sugar intake. Additionally, since tagatose has superior stability against heat and pH, with a boiling point of 134° C. and a pH of 2-7, it is not readily broken down, unlike most artificial sweeteners. It has physical and chemical properties very similar to those of sugar and is an important sugar substitute because it is a ketose exhibiting the characteristic of browning, which is very similar to that of fructose.

For these reasons, tagatose is drawing attentions as a functional sugar such as a food supplement or a diet sweetener. Therefore, there is a growing need for the development of a method for effectively producing tagatose in the food industry. It is because tagatose is a rare sugar included in trace amounts in dairy products or some plants and it cannot be synthesized chemically. It was recently reported that L-arabinose isomerase converts L-arabinose into L-ribulose and D-galactose into tagatose (patent document 1). At present, tagatose is being produced by isomerization of galactose via bioconversion using L-arabinose isomerase (patent document 2). Galactose is obtained from lactose. However, stable and consistent large-scale production is difficult because the supply and demand of lactose are unstable, lactose is more expensive than glucose or fructose, and its price varies greatly depending on the dairy market situation.

Therefore, methods for producing tagatose from glucose or fructose, which are advantageous in terms of stable supply and demand and low cost, as substrates using enzymes are being studied actively. But, the production of tagatose from fructose through a single enzyme reaction is not known yet. In addition, the conversion is hardly achieved and the production yield is very low with epimerases known thus far, as such single enzymes. Accordingly, a method for using red algae, the supply and demand of which are stable and the cost of which is low, as a substrate is necessary.

DISCLOSURE

Technical Problem

The present disclosure is directed to providing an enzyme complex which convers red algae-derived agar, as a marine biomass, into tagatose, and a method for preparing the same.

The present disclosure is also directed to providing a method for preparing tagatose by degrading red algae biomass using the enzyme complex.

Technical Solution

In an aspect, the present disclosure provides an agarase complex wherein: 1) a fusion protein 1 in which a monosaccharide convertase and a dockerin module are bound; 2) a fusion protein 2 in which agarase and a dockerin module are bound; and 3) a fusion protein 3 in which 3,6-anhydro-L-galactosidase and a dockerin module are bound; are linked via dockerin-cohesin binding by a mini scaffold protein including a cohesin module.

The monosaccharide convertase may be Lactobacillus-derived arabinose isomerase represented by an amino acid sequence of SEQ ID NO 1, although not being limited thereto.

The dockerin may be a cellulase-derived dockerin selected from a group consisting of endo-β-1,4-glucanase B, endo-β-1,4-xylanase B and exo-glucanase S. Specifically, the dockerin may have a base sequence of SEQ ID NO 35. But, considering genetic code degeneracy, a base sequence having 80% homology, specifically 85% homology, more specifically 90% homology, most specifically 95% homology, to the base sequence of SEQ ID NO 3 may also be included in the base sequence of the dockerin of the present disclosure, although not being limited thereto.

The agarase may be an agarase derived from one selected from a group consisting of Pseudomonas, Saccharophagus and Aleromonas, although not being limited thereto. More specifically, the agarase may be β-agarase, specifically one having a base sequence of SEQ ID NO 20. But, considering genetic code degeneracy, a base sequence having 80% homology, specifically 85% homology, more specifically 90% homology, most specifically 95% homology, to the base sequence of SEQ ID NO 20 may also be included in the base sequence of the β-agarase of the present disclosure, although not being limited thereto.

Specifically, the 3,6-anhydro-L-galactosidase may be derived from Zobellia and may have a base sequence of SEQ ID NO 36. But, considering genetic code degeneracy, a base sequence having 80% homology, specifically 85% homology, more specifically 90% homology, most specifically 95% homology, to the base sequence of SEQ ID NO 36 may also be included in the base sequence of the 3,6-anhydro-L-galactosidase of the present disclosure, although not being limited thereto.

The mini scaffold protein may be one selected from a group consisting of mini cellulose-binding protein A (mCbpA), Clostridium thermocellulm-derived mini scaffold protein (mCipA) and Clostridium cellulolyticum-derived mini scaffold protein (mCipC). More specifically, it may be mini cellulose-binding protein A (mCbpA) having a base sequence of SEQ ID NO 17. But, considering genetic code degeneracy, a base sequence having 80% homology, specifically 85% homology, more specifically 90% homology, most specifically 95% homology, to the base sequence of SEQ ID NO 17 may also be included in the base sequence of the mini cellulose-binding protein A (mCbpA) of the present disclosure, although not being limited thereto.

The enzyme complex may be agarase-3,6-anhydro-L-galactosidase-arabinose isomerase or β-agarase-3,6-anhydro-L-galactosidase-arabinose isomerase, although not being limited thereto.

In another aspect, the present disclosure provides a method for producing tagatose by degrading biomass using the agarase complex.

The biomass may be agar selected from purified agar, red algae-derived agar or agar present in red algae, although not being limited thereto.

In another aspect, the present disclosure provides a method for preparing an agarase complex, which includes: (a) a step of preparing a fusion protein 1 by linking a dockerin module to arabinose isomerase; (b) a step of preparing a fusion protein 2 by linking a dockerin module to β-agarase; (c) a step of preparing a fusion protein 3 by linking a dockerin module to 3,6-anhydro-L-galactosidase; (d) a step of preparing a mini scaffold protein having a cohesin module; and (e) a step of preparing an agarase complex by binding the cohesin module to the dockerin modules by quantifying the fusion proteins 1-3 and the mini scaffold protein of the step (d) to the same concentration of 2-20 nmol, more specifically 10 nmol, and the same proportion (1:1:1) and mixing them in a binding solution comprising 25 mM calcium chloride ($CaCl_2$)) and conducting reaction at 4° C. for 24 hours.

In the step (e), if the concentration of the fusion proteins and the mini scaffold protein is lower than 2 nmol or higher than 20 nmol, or if they are mixed with different proportions, the binding efficiency of the dockerin modules and the cohesin module is low.

In the present disclosure, "endoglucanase" refers to an enzyme which catalyzes the production of glucose polymers (cellobiose, cellotriose, etc.) by hydrolyzing the β-1,4-D-glycosidic bond of cellulose, and includes the enzyme endo-β-1,4-glucanase (EC 3.2.1.4, endoglucanase).

In the present disclosure, "cellulose-binding protein A" is a protein derived from Clostridium cellulovorans, and is a scaffold protein forming a cellulosome. Since the cellulose-binding protein has a carbohydrate-binding module which recognizes cellulose and binds strongly thereto, it allows easy access to a carbohydrate or cellulose for an enzyme binding to the protein. The cellulose-binding protein has a cohesin domain which binds specifically to the dockerin domain possessed by the enzyme of cellulosome-producing bacteria. Therefore, the number of the binding enzymes is determined by the number of cohesins.

In the present disclosure, the dockerin module of a bacterium in the genus *Clostridium* refers to a module possessed by a cellulosomal cellulase protein which forms the enzyme complex cellulosome through interaction with a cohesin module which is a portion of the cellulose-binding protein of a bacterium in the genus *Clostridium.*

In the present disclosure, "dockerin-cohesin binding" refers to the binding between the dockerin module of a cellulosome-forming enzyme and the cohesin module of a scaffold protein during the process whereby a cellulosome capable of degrading cellulose is formed (Bayer et al. Annual Review of Microbiol, 2004, 58, 521-554).

In the present disclosure, for the dockerin-cohesin binding, type I dockerin and cohesion of a strain producing a cellulosome may be used without limitation. Specifically, those derived from the same species may be used when considering species specificity. For example, dockerin type I derived from *Clostridium cellulovorans*, such as EngH, EngK, ExgS, EngL, ManA, EngM and EngN, and cohesin type I of cbpA derived from *Clostridium cellulovorans* may be used, although not being limited thereto.

In the present disclosure, a "vector" refers to a gene construct including an essential regulatory element operably linked so that the gene construct can be expressed as a target protein in a suitable host cell. When the vector is a replicable expression vector, it may include a replication origin which is a specific nucleic acid sequence at which replication is initiated.

In general, a plasmid vector is an extra-chromosomal circular double-stranded DNA, which is present in a cell and has various functions. It produces antibiotic-resistant substances and bacteriocins, thereby acting as an inhibitor to kill bacteria or host cells, and performs physiological functions such as pigment formation, compound decomposition and nitrogen fixation. It has a restriction enzyme site for insertion of foreign DNA fragments of up to about 10 kb in length.

The vector according to the present disclosure may contain a selection marker. The selection marker is for selecting cells transfected with the vector. Markers for conferring selectable phenotypes such as drug resistance, nutritional requirement, and resistance to cytotoxic agents or expression of surface proteins may be used. Under the environment treated with a selective agent, the transformed cells can be selected because only the cells expressing the selection marker survive. Representative examples of the selection marker include auxotrophic markers ura4, leu1, his3, etc. However, the types of the marker that can be used in the present disclosure are not limited to those examples.

The vector related with the present disclosure includes a plasmid vector (e.g., pSC101, ColE1, pBR322, pUC8/9, pHC79, pUC19, etc.), a cosmid vector, a bacteriophage vector (e.g., gt4B, -Charon, z1, M13, etc.), a viral vector, etc., although not being limited thereto.

A plasmid used as a vector and capable of inserting relatively small DNA fragments only, which is the major drawback of a bacteriophage, can clone larger DNA fragments using a cosmid, which is a manipulated hybrid of a plasmid and a phage DNA.

There is a cos site which is packed into a phage particle, and it has a gene that can select the plasmid and the start point of replication of the plasmid replicated in the bacterial host. Like a bacteriophage vector, it is packed in a protein envelope in vitro. But, once the packed DNA has infected the *E. coli* host cell, the DNA is replicated in the plasmid form rather than the bacteriophage DNA and is not lysed. Its size is 2.5 kb. After the host cell has been infected and packaged and the cos site has been split from 37 kb to 52 kb, a foreign DNA is housed as an insert. Generally, 35-45 kb can be cloned into a cosmid vector.

A phage, which is a common form of the bacteriophage vector, originates from a 50-kb double-stranded wild-type genome with cohesive termini or cos with complementary ends of single-stranded 12 nucleotides capable of forming base pairs. In the lytic pathway, new viruses are replicated in the host cell, and the host cell is lysed after the offspring viruses are released. This type of DNA accommodates up to 5% of the genome, i.e., 3 kb of its total 52 kb, and a vector that creates a space for foreign DNA is free of non-essential DNA fragments.

The viral vector may be a vector derived from a retrovirus, e.g., human immunodeficiency virus (HIV), murine leukemia virus (MLV), avian sarcoma and leukosis virus (ASLV), spleen necrosis virus (SNV), Rous sarcoma virus (RSV), mouse mammary tumor virus (MMTV), etc., adenovirus, an adeno-associated virus (AAV), herpes simplex virus, etc., although not being limited thereto.

In the present disclosure, a "primer" refers to a single-stranded oligonucleotide. It includes a ribonucleotide and may be specifically a deoxyribonucleotide. The primer is hybridized or annealed to a portion of a template to form a double-stranded structure. In the present disclosure, a primer may be hybridized or annealed to an NGS adapter sequence. The annealing refers to apposition of an oligonucleotide or a nucleic acid to a template nucleic acid, and the apposition refers to formation of a nucleic acid molecule complementary to the template nucleic acid or a part thereof by polymerization of nucleotides using a polymerase. The hybridization refers to formation of a duplex structure by pairing of two single-stranded nucleic acids with complementary base sequences. The primer may serve as a starting point of synthesis under conditions for inducing the synthesis of an elongated product of the primer complementary to the template.

In the present disclosure "operably linked" means that a nucleotide sequence encoding a target protein is linked in such a way as to perform general functions. The operable linkage to a recombinant vector may be achieved using a genetic recombination technique well known in the art, and site-specific DNA cleavage and ligation may be easily achieved using enzymes generally known in the art.

In the present disclosure, the "regulatory element" refers to an undecoded nucleic acid sequence that helps to improve the transcription, translation or expression of a nucleic acid sequence encoding a protein or affects the same. The expression vector of the present disclosure necessarily includes the genetic circuit of the present disclosure as the regulatory element, and may include an expression control sequence that may affect protein expression, e.g., a start codon, a stop codon, a polyadenylation signal, an enhancer, a signal sequence for membrane targeting or secretion, etc.

In the present disclosure, the "host cell" refers to a cell which parasitizes another microorganism or gene and supplies nutrition thereto, and means a cell in which a vector is transformed into the host cell to exert various genetic or molecular effects in the host cell. A foreign DNA such as a vector may be inserted into the host cell when the cell is in a competent state capable of accepting the foreign DNA. When a vector is successfully introduced into a host cell, the genetic trait of the vector is provided to the host cell.

Specifically, the host microorganism of the present disclosure may be Gram-negative bacteria. The Gram-negative bacteria include bacteria in the genus *Salmonella* (*Salmonella* sp.), the genus *Acinebacter* (*Acinebacter* sp.), the genus *Escherichia* (*Escherichia* sp.), the genus *Pseudomonas* (*Pseudomonas* sp.), the genus *Klebsiella* (*Klebsiella* sp.), etc., e.g., *Salmonella typhimurium, Acinebacter calcoaceticus, E. coli, Pseudomonas aeruginosa, Klebsiella aerogenes, Acinetobacter baumannii, Klebsiella pneumoniae*, etc. However, the host cell that can be transformed with the vector of the present disclosure is not limited to those described above.

Transformation can be used to introduce a vector into a host cell. The "transformation" refers to a phenomenon in which DNA is introduced into a host and the DNA becomes replicable as a factor of chromosome or by chromosomal integration. The introduction of the foreign DNA into the cell results in artificial genetic change. Any transformation method can be used for the transformation according to common methods in the art. In general, the transformation method includes $CaCl_2$ precipitation, the Hanahan method in which the effect of the $CaCl_2$ method is improved by using DMSO (dimethyl sulfoxide), electroporation, calcium phosphate precipitation, protoplast fusion, agitation using silicon carbide fibers, Agrobacteria-mediated transformation, transformation using polyethylene glycol (PEG), dextran sulfate-, lipofectamine- and drying/inhibition-mediated transformation, etc. The method for transforming the plasmid of the present disclosure is not limited to the above examples, and the transformation methods commonly used in the art can be used without limitation.

The host cell transformed by the above-described method can be cultured as necessary via culturing methods commonly used in the art, and the culture medium and culturing period can be selected as desired by those skilled in the art.

Specifically, *E. coli* cultured in an LB (Luria-Bertani) medium for 8 hours may be cultured further for 12 hours to induce the production of proteins from recombinant genes. As the medium, various media that can be generally used in the art may be used.

Advantageous Effects

A method for producing tagatose according to the present disclosure is environment-friendly because only an enzyme obtained from a microorganism is used, and the production efficiency can be maximized whereas the production cost is reduced greatly because only a simple process of enzyme complex formation is necessary and an inexpensive biomass substrate is used. That is to say, by using the enzyme complex according to the present disclosure, agar obtained from the marine biomass red algae can be degraded effectively and galactose obtained as a degradation product can be converted into tagatose, which is a useful rare sugar, effectively.

BRIEF DESCRIPTION OF DRAWINGS

FIG. 1A and FIG. 1B show schematic views of a recombinant vector prepared according to the present disclosure (1A) and the expression of the vector in *E. coli* (1B).

FIG. 2 shows the activity of converting D-galactose to D-tagatose using an enzyme complex prepared according to the present disclosure.

FIG. 3 shows the activity of degrading agar and converting to tagatose of an enzyme complex prepared according to the present disclosure.

FIG. 4A and FIG. 4B show the activity of an enzyme complex prepared according to the present disclosure for substrates (4A: purified gar, 4B: agar).

BEST MODE

Hereinafter, the present disclosure will be described in detail through examples. However, the following examples are for illustrative purposes only and it will be apparent to those of ordinary skill in the art that the scope of the present disclosure is not limited by the examples.

EXAMPLES

Example 1. Expression Vector for Novel Enzyme Complex

In order to prepare a novel enzyme complex, a vector and a transformant including genes encoding the components of the enzyme complex were prepared.

1.1 *Lactobacillus*-Derived Arabinose Isomerase Expression Vector

For cloning of proteins for producing tagatose from an agar degradation product as a substrate, a vector expressing the arabinose isomerase gene was prepared first.

Referring to the base sequence of the arabinose isomerase (LsAraA) gene from the gDNA of bacteria in the genus *Lactobacillus*, primers were designed and synthesized such that the Sac I recognition sequence was inserted to the 5' end of a forward primer (SEQ ID NO 2) and the Hind III recognition sequence was inserted to the 5' end of a reverse primer (SEQ ID NO 3). Then, PCR was conducted using the synthesized primers. As a result, the PCR band of the 1479-bp arabinose isomerase (LsAraA) gene (SEQ ID NO 4) was observed (result not shown).

Then, the arabinose isomerase (LsAraA) gene was purified, ligated to the *E. coli* expression vector pColdII, and transformed into *E. coli* BL21 using the restriction enzymes Sac I and Hind III. The transformant was named BL21/LsAraA. Then, the ligated recombinant plasmid DNA was isolated from the transformant. The recombinant plasmid vector was named pColdII LsAraA.

1.2 Preparation of *Lactobacillus*-Derived Arabinose Isomerase Expression Vector and Transformant Fused with Dockerin An expression vector and a transformant wherein the arabinose isomerase enzyme of Example 1.1 was fused with a cellulase-derived dockerin domain were prepared.

A. Arabinose Isomerase Gene Fragment

Referring to the base sequence of the arabinose isomerase (LsAraA) gene from the genomic DNA of bacteria in the genus *Lactobacillus*, primers were designed and synthesized such that the Sac I recognition sequence was inserted to the 5' end of a forward primer (SEQ ID NO 5) and the 10-bp sequence at the N-terminal of the dockerin moiety of the endo-β-1,4-glucanase B gene derived from *Clostridium cellulovorans* was inserted to the 5' end of a reverse primer (SEQ ID NO 6). Then, PCR was conducted using the synthesized primers. As a result, the PCR bands of the Sac I recognition sequence capable of recognizing the dockerin moiety and the 1521-bp arabinose isomerase (LsAraA) gene were observed (result not shown).

B. Dockerin Fragment

In addition, referring to the base sequence of the dockerin moiety of the endo-β-1,4-glucanase B gene from the gDNA of *Clostridium cellulovorans*, primers were designed and synthesized such that the 10-bp sequence at the C-terminal of the arabinose isomerase (LsAraA) gene was inserted to the 5' end of a forward primer (SEQ ID NO 7) and the Kpn I recognition sequence was inserted to the 5' end of a reverse primer (SEQ ID NO 8).

The 10-bp sequence at the N-terminal of the dockerin moiety of the endo-β-1,4-glucanase B gene is represented by SEQ ID NO 9, and the 10-bp sequence at the C-terminal of the arabinose isomerase (LsAraA) gene is represented by SEQ ID NO 10.

Then, PCR was conducted using the synthesized primers. As a result, the PCR band of the dockerin moiety of the 195-bp endo-β-1,4-glucanase B gene (SEQ ID NO 11) was observed.

C. Preparation of Fusion Protein Expression Vector and Transformant

The gene amplification product of the arabinose isomerase (LsAraA) gene and the dockerin domain of cellulase obtained above was subjected to electrophoresis on 0.8% agarose gel, and the DNA fragments on the agarose gel were recovered using a gel extraction kit (GeneAll).

Using the two recovered DNA fragments, primers were designed and synthesized such that the Sac I recognition sequence was inserted to the 5' end of a forward primer (SEQ ID NO 12) and the Kpn I recognition sequence was inserted to the 5' end of a reverse primer (SEQ ID NO 13).

Then, overlap PCR was conducted using the recovered DNA fragments in order to link the arabinose isomerase (LsAraA) gene with the dockerin domain of cellulase. The overlap PCR reaction was conducted at 94° C. for 2 minutes followed by 10 cycles of 94° C. for 30 seconds, 52° C. for 25 minutes and 72° C. for 5 minutes, finally at 72° C. for 5 minutes. As a result of the PCR, a PCR band of the bacterium-derived expansin gene linked with the 1671-bp dockerin domain of cellulase (SEQ ID NO 14) was observed (result not shown).

After purifying the dockerin-fused arabinose isomerase LsAraA Doc gene, a recombinant expression vector was prepared by ligating the SacI and KpnI restriction enzyme sequences to the E. coli expression vector pColdII. Then, a transformant was prepared by transforming E. coli BL21 with the expression vector. Then, the plasmid DNA of the ligated recombinant expression vector was isolated from the transformant. The recombinant vector was named pColdII LsAraA-Doc (FIG. 1A), and the E. coli transformant was named BL21/LsAraA-Doc.

1.3 Confirmation of Expression of Novel Enzyme Complex in Transformant

In order to investigate protein expression in the transformant obtained in Example 1, purification and SDS-PAGE were performed using His-Tag.

Expression was induced in the E. coli transformant with IPTG at 16° C. for 12 hours using 1 mM IPTG. After creating a condition where the arabinose isomerase enzyme and the dockerin-fused arabinose isomerase enzyme can be expressed, the cells were cultured at 16° C. for 12 hours under shaking and then centrifuged. The cells were lysed by sonication and then centrifuged. Proteins obtained by concentrating the supernatant (Millipore, Amicon 10 kDa cutoff) was loaded onto SDS-PAGE. Then, the proteins were analyzed by western blot using the His-tag attached at the N-terminal. As a result, the arabinose isomerase enzyme and the dockerin-fused arabinose isomerase enzyme were observed at the expected locations (FIG. 1B).

Example 2. Construction of Arabinose Isomerase Enzyme Complex with Mini Cellulose-Binding Protein Linked and Analysis of Activity for Galactose Substrate 2.1 Construction of Expression Vector for Enzyme Complex For cloning of the mini cellulose-binding protein A gene having a cellulose-binding module (CBM) and two cohesin modules of cellulose-binding protein A which is the primary scaffolding subunit of Clostridium cellulovorans, primers were synthesized such that the BamHI recognition sequence (ggatcc) was inserted to the 5' end of a forward primer (SEQ ID NO 15) and the XhoI recognition sequence (ctcgag) was inserted to the 5' end of a reverse primer (SEQ ID NO 16) referring to the base sequence. As a result, a 1659-bp PCR band containing the mCbpA gene (SEQ ID NO 17) which is a part of the cellulose-binding protein A gene derived from Clostridium cellulovorans was observed (result not shown).

2.2 Confirmation of Enzyme Complex Formation

In order to confirm the formation of a complex through binding between the arabinose isomerase linked with the dockerin module of the endo-β-1,4-glucanase B gene and the mini cellulose-binding protein mCbpA, the two proteins were mixed and incubated at low temperature and then incubated to induce complex formation. For the complex formation, the mini scaffold protein and the arabinose isomerase were quantitated both to 10 nmol and then mixed in a binding solution containing 25 mM $CaCl_2$). For binding between the cohesin module and the dockerin module, reaction was conducted at 4° C. for 24 hours.

The formation of a complex through binding between the arabinose isomerase enzyme linked with the dockerin module of the endo-β-1,4-glucanase B gene and the mini cellulose-binding protein mCbpA was confirmed by measuring increased tagatose conversion activity. As a result of measuring tagatose conversion activity for mCbpA, arabinose isomerase and arabinose isomerase-mCbpA using galactose as a substrate, the degradation activity was increased in the order of mCbpA (M), arabinose isomerase (LsAraA, L) and arabinose isomerase-mCbpA (LM) (FIG. 2). Because mCbpA is an inactive protein with no tagatose conversion activity, the increased activity is due to the enzyme complex formation.

In addition, since the fusion protein with the mini cellulose-binding protein mCbpA showed higher tagatose conversion activity than arabinose isomerase (LsAraA) alone, it was confirmed that mCbpA improves the tagatose conversion activity of arabinose isomerase (LsAraA).

Example 3. Construction of Enzyme Complex Expression Vector for Agar Degradation Product For production of tagatose from the less expensive substrate agar, a fusion protein including agarase and dockerin and a fusion protein including 3,6-anhydro-L-galactosidase and dockerin were designed.

3.1 Preparation of Enzyme Complex (Fusion of β-Agarase and Dockerin)

A. Isolation of β-Agarase Gene

In order to bind β-agarase to the dockerin gene, primers for processing both ends of the β-agarase gene were prepared. Primers were designed and synthesized such that the Sac I recognition sequence was inserted to the 5' end of a forward primer (SEQ ID NO 18) and the referring to the base sequence of the β-agarase AgaB gene from the genomic DNA of bacteria in the genus Zobellia and a 10-bp sequence at the N-terminal was inserted to the 5' end of a reverse primer (SEQ ID NO 19) referring to the base sequence of the dockerin moiety of the endo-β-1,4-glucanase B gene derived from Clostridium cellulovorans. Then, PCR was conducted using the synthesized primers. The PCR reaction was conducted at 95° C. for 5 minutes, followed by 30 cycles of 95° C. for 1 minute, 52° C. for 1 minute and 72° C. for 2 minutes, finally at 72° C. for 5 minutes. As a result, a 1005-bp PCR band containing the β-agarase gene (SEQ ID NO 20) was observed (result not shown).

B. Processing of β-Agarase Gene

Referring to the base sequence of the dockerin moiety of the endo-β-1,4-glucanase B gene from the gDNA of *Clostridium cellulovorans*, primers were designed and synthesized such that a 10-bp sequence at the C-terminal of the β-agarase AgaB gene from the genomic DNA of bacteria in the genus *Zobellia* was inserted to the 5' end of a forward primer (SEQ ID NO 21) and the NotI recognition sequence was inserted to the 5' end of a reverse primer (SEQ ID NO 22). Then, PCR was conducted using the synthesized primers. The PCR reaction was conducted at 95° C. for 5 minutes, followed by 30 cycles of 95° C. for 1 minute, 52° C. for 1 minute and 72° C. for 2 minutes, finally at 72° C. for 5 minutes. As a result, a 211-bp PCR band containing the dockerin moiety of the endo-β-1,4-glucanase B gene (SEQ ID NO 23) was observed (result not shown).

C. Construction of Enzyme Complex (β Agarase-Dockerin) Expression Vector

The gene amplification product of the β agarase AgaB gene and the dockerin domain of the cellulase obtained above was subjected to electrophoresis on 0.8% agarose gel. The DNA fragments on the agarose gel were recovered using a gel extraction kit (GeneAll).

Then, overlap PCR was conducted using the recovered DNA fragments in order to link the β agarase AgaB gene with the dockerin domain of cellulase. The overlap PCR reaction was conducted at 94° C. for 2 minutes, followed by 10 cycles of 94° C. for 30 seconds, 52° C. for 25 minutes and 72° C. for 5 minutes, finally at 72° C. for 5 minutes. From the recovered two DNA fragments, primers were designed and synthesized such that the SacI recognition sequence was inserted to the 5' end of a forward primer (SEQ ID NO 24) and the NotI recognition sequence was inserted to the 5' end of a reverse primer (SEQ ID NO 25). After conducting PCR at 95° C. for 5 minutes, followed by 30 cycles of 95° C. for 1 minute, 52° C. for 1 minute and 72° C. for 2 minutes, finally at 72° C. for 5 minutes, a 1225-bp PCR band containing the chimeric β-agarase AgaB gene derived from *Zobellia galactanivorans* with the dockerin domain of cellulase linked (SEQ ID NO 20) was observed as the PCT product (result not shown).

Then, after cleaving the dockerin-fused chimeric β-agarase AgaB gene and the AgaB Doc gene, *E. coli* BL21 was transformed by ligating to the *E. coli* expression vector pET22b(+) with SacI and NotI. Then, the ligated recombinant plasmid DNA was isolated from the transformant. The recombinant vector was named pET22(+) AgaB-Doc, and the *E. coli* transformant was named BL21/AgaB-Doc.

3.2 Preparation of Enzyme Complex (Fusion of 3,6-Anhydro-L-Galactosidase and Dockerin)

A. Isolation of 3,6-Anhydro-L-Galactosidase Gene

For cloning of the dockerin domain of cellulase for 3,6-anhydro-L-galactosidase with dockerin bound, primers were designed and synthesized such that the EcoRI recognition sequence was inserted to the 5' end of a forward primer (SEQ ID NO 27) referring to the base sequence of the 3,6-anhydro-L-galactosidase AhgA gene from the genomic DNA of bacteria in the genus *Zobellia* and a 10-bp sequence at the N-terminal was inserted to the 5' end of a reverse primer (SEQ ID NO 28) referring to the base sequence of the dockerin moiety of the endo-β-1,4-glucanase B gene derived from *Clostridium cellulovorans*. Then, PCR was conducted using the synthesized primers. The PCR reaction was conducted at 95° C. for 5 minutes, followed by 30 cycles of 95° C. for 1 minute, 52° C. for 1 minute and 72° C. for 2 minutes, finally at 72° C. for 5 minutes. As a result, a 1224-bp PCR band containing 3,6-anhydro-L-galactosidase (SEQ ID NO 29) was observed (result not shown).

B. Isolation of Dockerin Gene

Referring to the base sequence of the dockerin moiety of the endo-β-1,4-glucanase B gene from the gDNA of *Clostridium cellulovorans*, primers were designed and synthesized such that a 10-bp sequence at the C-terminal of the 3,6-anhydro-L-galactosidase AhgA gene from the genomic DNA of bacteria in the genus *Zobellia* was inserted to the 5' end of a forward primer (SEQ ID NO 30) and the Hind III recognition sequence was inserted to the 5' end of a reverse primer (SEQ ID NO 31). Then, PCR was conducted using the synthesized primers. The PCR reaction was conducted at 95° C. for 5 minutes, followed by 30 cycles of 95° C. for 1 minute, 52° C. for 1 minute and 72° C. for 2 minutes, finally at 72° C. for 5 minutes. As a result, a 211-bp PCR band containing the dockerin moiety of the endo-β-1,4-glucanase B gene (SEQ ID NO 32) was observed.

C. Construction of Enzyme Complex (Galactosidase-Dockerin) Expression Vector

The gene amplification product of the 3,6-anhydro-L-galactosidase AhgA gene and the dockerin domain of cellulase obtained above was subjected to electrophoresis on 0.8% agarose gel, and the DNA fragments on the agarose gel were recovered using a gel extraction kit (GeneAll).

Then, overlap PCR was conducted using the recovered DNA fragments in order to link the 3,6-anhydro-L-galactosidase AhgA gene and the dockerin domain of cellulase. From the recovered two DNA fragments, primers were designed and synthesized such that the EcoR I recognition sequence was inserted to the 5' end of a forward primer (SEQ ID NO 33) and the HindIII recognition sequence was inserted to the 5' end of a reverse primer (SEQ ID NO 34). After conducting PCR at 95° C. for 5 minutes, followed by 30 cycles of 95° C. for 1 minute, 52° C. for 1 minute and 72° C. for 2 minutes, finally at 72° C. for 5 minutes, a 1383-bp PCR band containing the chimeric 3,6-anhydro-L-galactosidase AhgA gene (SEQ ID NO 36) derived from *Zobeffia galactanivorans* with the dockerin domain of cellulase linked (SEQ ID NO 35) was observed (result not shown).

Example 4. Analysis of Activity of Enzyme Complex (Dockerin Complex) for Agar Degradation Product Expression was induced in the BL21/AgaB-Doc and BL21/AhgA-Doc recombinant strains using 1 mM IPTG at 16° C. for 12 hours. After centrifugation, the cells were lysed by sonication and then centrifuged. Proteins were obtained by concentrating the supernatant (Millipore, Amicon 10 kDa cutoff).

Tagatose conversion activity was investigated using agar as a substrate. More specifically, purified agar was degraded using dockerin-agarase (cAgaB), dockerin-3,6-anhydro-L-galactosidase (cAhgA), dockerin-agarase (cAgaB) or dockerin-3,6-anhydro-L-galactosidase (cAhgA), and then tagatose conversion activity was analyzed after adding the dockerin-arabinose isomerase fusion protein (LsAraA).

As seen from FIG. 3, the combination of dockerin-agarase (cAgaB) and dockerin-3,6-anhydro-L-galactosidase (cAhgA), i.e., cAgaB/cAhgA+LsAraA, showed higher tagatose conversion activity for the purified agar.

Example 5. Preparation of Enzyme Complex

Finally, the enzyme complex according to the present disclosure (β-agarase-3,6-anhydro-L-galactosidase-arabinose isomerase) was prepared as follows. The mini scaffold protein, β-agarase, 3,6-anhydro-L-galactosidase and arabinose isomerase were quantitated to the same concentration of 10 nmol and same proportion and then mixed in a binding solution containing 25 mM $CaCl_2$). Then, reaction was conducted at 4° C. for 24 hours for binding between the cohesin module and the dockerin module.

Example 6. Analysis of Activity of Enzyme Complex for Various Agar Substrates

The activity of the complexes consisting of β-agarase-3,6-anhydro-L-galactosidase-arabinose isomerase and mCbpA with various compositions was analyzed using various agar (purified agar and red algae agar) substrates.

As seen from FIG. 4A and FIG. 4B, the β-agarase-3,6-anhydro-L-galactosidase-arabinose isomerase enzyme complex showed higher tagatose conversion efficiency than agarase or arabinose isomerase alone for both the purified agar (4A) and the red algae agar (4B). In the figure, C stands for control, B for β-agarase, A for 3,6-anhydro-L-galactosidase, M for mini scaffold protein, and L for arabinose isomerase.

The invention claimed is:

1. An agarase complex comprising:
a mini scaffold protein comprising a cohesin module;
a first fusion protein in which a monosaccharide convertase and a first dockerin module are bound;
a second fusion protein in which agarase and a second dockerin module are bound; and
a third fusion protein in which 3,6-anhydro-L-galactosidase and a third dockerin module are bound,
wherein the first, the second and the third fusion proteins are linked to the mini scaffold protein via dockerin-cohesin binding,
wherein the monosaccharide convertase is arabinose isomerase derived from *Lactobacillus*, and
wherein the arabinose isomerase comprises the amino acid sequence of SEQ ID NO 1.

2. The enzyme complex according to claim 1, wherein the first, the second, and the third dockerins are derived from cellulase.

3. The enzyme complex according to claim 2, wherein the first, the second, and the third dockerins are encoded by the nucleotide sequence of SEQ ID NO 35.

4. The enzyme complex according to claim 2, wherein the cellulase is selected from the group consisting of endo-β-1,4-glucanase B, endo-β-1,4-xylanase B and exo-glucanase S.

5. The enzyme complex according to claim 1, wherein the agarase is derived from one selected from the group consisting of *Pseudomonas, Saccharophagus* and Aleromonas.

6. The enzyme complex according to claim 5, wherein the agarase is β-agarase.

7. The enzyme complex according to claim 6, wherein the β-agarase is encoded by the nucleotide sequence of SEQ ID NO 20.

8. The enzyme complex according to claim 1, wherein the 3,6-anhydro-L-galactosidase is derived from *Zobellia*.

9. The enzyme complex according to claim 8, wherein the 3,6-anhydro-L-galactosidase is encoded by the nucleotide sequence of SEQ ID NO 36.

10. The enzyme complex according to claim 1, wherein the mini scaffold protein is one selected from the group consisting of mini cellulose-binding protein A (mCbpA), *Clostridium thermocellum*-derived mini scaffold protein (mCipA) and *Clostridium cellulolyticum*-derived mini scaffold protein (mCipC).

11. The enzyme complex according to claim 10, wherein the mini scaffold protein is mini cellulose-binding protein A (mCbpA).

12. The enzyme complex according to claim 11, wherein the mini cellulose-binding protein A is encoded by the nucleotide sequence of SEQ ID NO 17.

13. A method for producing tagatose by degrading biomass using the enzyme complex according to claim 1.

14. The method according to claim 13, wherein the biomass is agar derived from red algae.

15. A method for preparing an enzyme complex, comprising:
   preparing a first fusion protein by linking a first dockerin module to an arabinose isomerase;
   preparing a second fusion protein by linking a second dockerin module to a β-agarase;
   preparing a third fusion protein by linking a third dockerin module to a 3,6-anhydro-L-galactosidase;
   preparing a mini scaffold protein having a cohesin module; and
   preparing the enzyme complex by binding the cohesin module to the first, the second, and the third dockerin modules by quantifying the first, the second, and the third fusion proteins and the mini scaffold protein to a same concentration and proportion and mixing them in a binding solution comprising 25 mM calcium chloride ($CaCl_2$)),
   wherein the arabinose isomerase comprises the amino acid sequence of SEQ ID NO 1.

* * * * *